US00PP10398P

United States Patent [19]

Trees

[11] Patent Number: Plant 10,398

[45] Date of Patent: May 12, 1998

[54] GERANIUM PLANT NAMED 'BFP-484 WHITE'

[75] Inventor: Scott C. Trees, Arroyo Grande, Calif.

[73] Assignee: Ball Horticultural Company, West Chicago, Ill.

[21] Appl. No.: 701,150

[22] Filed: Aug. 21, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 8,284 6/1993 Trees ..... Plt./87.12

P.P. 9,971 7/1997 Hofmann ..... Plt./87.12

P.P. 10,012 8/1997 Lemon ..... Plt./87.12

*Primary Examiner*—Howard J. Locker

*Assistant Examiner*—Kent L. Bell

*Attorney, Agent, or Firm*—Burns, Doane, Swecker & Mathis, L.L.P.

[57] ABSTRACT

The new and distinct *Pelargonium×hortorum* cultivar named 'BFP-484 White' is provided. This new Zonal Geranium was the result of a controlled breeding program wherein a plant designated 995B-2 (non-patented in the United States) was pollinated by the 'Jazz' cultivar (non-patented in the United States). The new cultivar forms attractive pure white florets. Medium green foliage is well retained during shipment. The growth habit is vigorous self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-484 White'.

The new cultivar is a product of a planned breeding program which had the objective of the creation of a Geranium cultivar that exhibits uniform flowers, medium green foliage, a vigorous self-branching growth habit that requires no growth regulator, a propensity for rapid rooting, and stable foliage coloration during shipment.

The breeding program that resulted in the production of the new cultivar of the present invention was carried out in a controlled environment during 1990 at Arroyo Grande, Calif., U.S.A. The female parent (i.e., seed parent) was a plant designated 955B-2 (non-patented in the United States) which exhibits semi-double pink florets with dark green foliage. The male parent (i.e., pollen parent) was the 'Jazz' cultivar (non-patented in the United States) which exhibits semi-double melon-colored florets with medium green foliage. The parentage of the new 'BFP-484 White' cultivar can be summarized as follows:

955B-2×'Jazz'.

'BFP-48 White' was discovered and selected during 1990 as a highyly distinctive flowering plant from among the progeny of the stated cross at Arroyo Grande, Calif., U.S.A. This plant was initially designated BFP-484.

It was found that the new cultivar of the present invention:

(a) exhibits attractive semi-double pure white florets,
(b) forms attractive medium green foliage with slight zonation, and
(c) exhibits a vigorous self-branching growth habit in the absence of a growth regulator.

After senescence the flowers abscice and drop. To date, observations of the new 'BFP-484 White' cultivar have not demonstrated resistance to Botrytis or any other specific disease.

The first act of asexual reproduction of 'BFP-484 White' cultivar was accomplished when vegetative cuttings were taken from the initial selection in a controlled environment at Arroyo Grande, Calif., U.S.A by a technician working under the direction and supervision of the originator of the new cultivar. Horticultural examination of plants resulting from such asexual propagation during 1991 has demonstrated that the combination of unique characteristics as herein described for the 'BFP-484 White' cultivar is fixed and is retained through successive generations of such asexual reproduction.

The new 'BFP-484 White' cultivar has not been observed under all possible environmental conditions. Accordingly, the described phenotype may vary somewhat with variations in the environment, such as temperature, light intensity, and day length.

Of the many commercial cultivars, the 'BSR-177 White' cultivar (U.S. Plant Pat. No. 8,284) is considered to be the most similar to the new cultivar of the present invention. The 'BSR-177 White' cultivar is marketed under the Showcase White trademark. When the new cultivar of the present invention is compared to the 'BSR-177 White' cultivar, it is found that the new 'BFP-484 White' cultivar exhibits purer white non-blushing florets vs. florets that include a blush of light pink under cool growing conditions, a more vigorous growth habit wherein the height commonly is approximately 22 to 24.5 cm. vs. approximately 16 to 19.5 cm., and a larger umbel diameter commonly of approximately 9 to 11 cm. vs. approximately 9 to 9.4 cm.

The new cultivar of the present invention is being marketed under the Designer trademark.

BRIEF DESCRIPTION OF THE PHOTOGRAPH

The accompanying photograph shows the new 'BFP-484 White' cultivar with colors being as nearly true as it is reasonably possible to make the same in a color illustration of this character. The plant was being grown in a greenhouse at West Chicago, Ill., U.S.A. The general appearance of the overall plant including the flower and foliage characteristics is illustrated.

DETAILED DESCRIPTION

The following observations, measurements and comparisons describe plants grown in greenhouses located at West Chicago, Ill., U.S.A., under conditions which approximate those generally used in commercial practice. In the following description, color references are made to the R.H.S. Colour Chart of The Royal Horticultural Society, London, England. The color values were determined on September 22nd, under natural light conditions of 200 footcandles.

Classification:

*Botanical.*—*Pelargonium×hortorum* Bailey, cv. 'BFP-484 White'.

*Commercial.*—Zonal Geranium.

Inflorescence

A. Umbel:

*Average diameter.*—Approximately 9 to 11 cm. compared to approximately 9 to 9.4 cm. for the 'BSR-177 White'.

*Average depth.*—Approximately 5.5 to 8 cm. compared to approximately 5 to 6 cm. for the 'BSR-177 White' cultivar.

*Peduncle length.*—Approximately 15 to 17 cm. compared to approximately 11 to 13 cm. for the 'BSR-177 White' cultivar.

*Pedicel length.*—Approximately 3.5 to 4 cm. compared to approximately 3.4 to 4 cm. for the 'BSR-177 White' cultivar.

*Number of umbels plant.*—When grown in a 10 cm. pot at 9 weeks after the sticking of a rooted cutting, there commonly are approximately 3 to 4 umbels per plant. The 'BSR-177 White' cultivar also commonly forms approximately the same number of umbels per plant .

*Number of florets/umbel.*—When grown in 10 cm. pots at 9 weeks, approximately 22 to 29 florets per umbel commonly are formed. This compares to approximately 25 to 26 florets per umbel for the 'BSR-177 White' cultivar under the same growing conditions.

B. Corolla:

*Buds.*—Elliptical to round in configuration, initially light green and changing to pure white at the time of opening, and approximately 9 to 10 mm. in length and approximately 6 to 6.5 mm. in width.

*Pedicels.*—Commonly approximately 3.5 to 4 cm. in length and curved which commonly causes the buds to point substantially downward (as illustrated).

*Average diameter.*—Approximately 4.5 to 4.8 cm. compared to approximately 4.9 to 5 cm. for the 'BSR-177 White' cultivar.

*Form.*—Both the 'BFP-484 White' cultivar and the 'BSR-177 White' cultivar are semi-double commonly with at least one petaloid.

*Petals.*—Spatulate shaped, satiny and smooth. Commonly approximately 7 to 9 petals are present per floret. This compares to approximately 5 to 6 petals per floret for the 'BSR-177 White' cultivar.

*Number of petaloids.*—Commonly forms approximately 1 to 4 petaloids per floret whereas the 'BSR-177 White' cultivar occasionally forms only about 1 petaloid per floret.

*Color.*—General tonality from a distance of three meters: White. Adaxial: White Group 155D for both the 'BFP-484 White' cultivar and the 'BSR-177 White' cultivar. Abaxial: White Group 155D for both the 'BFP-484 White' cultivar and the 'BSR-177 White' cultivar. However, unlike the 'BFP-484 White' cultivar, the florets of the 'BSR-177 White' cultivar sometimes exhibit a tendency to assume a light pink blush when cooler growing conditions are experienced.

C. Reproductive organs:

*Androecium.*—The anthers are commonly approximately 1.5 to 2 mm. in length. The pollen color is Orange Group 28B for the 'BFP-484 White' cultivar and Orange Group 25A for the 'BSR-177 White' cultivar. The filaments are approximately 6 to 7 mm. in length.

*Gynoecium.*—The pistil length commonly is approximately 12 mm. There is a single stigma which commonly has a length of approximately 6 mm. which commonly branches into 5 parts, and the style length is approximately 4 mm.

*Fertility.*—Commonly does not produce fruits in the absence of mechanical fertilization.

D. Spring flowering response period: Approximately 6 to 7 weeks from rooted cuttings under standard greenhouse conditions.

E. Outdoor flower production: Freely flowering under outdoor growing condiitons with substantially continuous blooming.

F. Durability: Ships well.

Plant

A. Foliage: Medium green with slight zonation. The leaves are thick and more pubescent than those of the 'BSR-177 White' cultivar. The rib and venation is palmate.

*Form.*—Reniform, with a cordate base.

*Margin.*—Bi-crenate and somewhat undulate.

*Color.*—Adaxial: Yellow-Green Group 146B with an outer edge of Yellow-Green Group 146A. This compares to Yellow-Green Group 146B for the 'BSR-177 White' cultivar. Abaxial: Yellow-Green Group 147B. This compares to Yellow-Green Group 146C for the 'BSR-177 White' cultivar.

*Size.*—Approximately 9 to 9.7 cm. in width at the widest point and approximately 7 to 8 cm. in length. This compares to approximately 9 to 9.5 cm in width at the widest point and approximately 7.8 to 8.9 cm. in length for the 'BSR-177 White' cultivar.

*Petioles.*—Commonly approximately 3.1 to 6 cm. in length.

B. General appearance and form:

*Internode length.*—Commonly varies from approximately 0.3 to 0.6 cm. This compares to approximately 1.4 to 2 cm. for the 'BSR-177 White' cultivar.

*Branching pattern.*—Freely basal branching. No pinching is required to obtain self-branching. A self-branching growth habit is observed in the absence of a growth regulator.

*Height.*—Approximately 22 to 24.5 cm. above a 10 cm. pot at 9 weeks under standard greenhouse conditions. This compares to approximately 16 to 19.5 cm. for the 'BSR-177 White' cultivar.

I claim:

1. A new and distinct cultivar of Geranium plant named 'BFP-484 White', substantially as herein shown and described, which:

(a) exhibits attractive semi-double pure white florets, (b) forms attractive medium green foliage with slight zonation, and (c) exhibits a vigorous self-branching growth habit in the absence of a growth regulator.

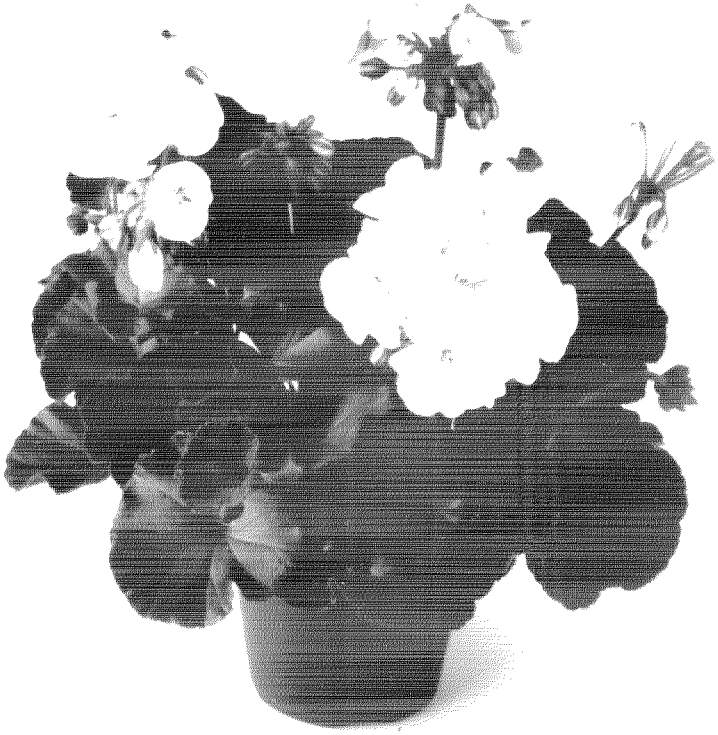

* * * * *